(12) United States Patent
Malmstrom et al.

(10) Patent No.: US 7,921,718 B2
(45) Date of Patent: Apr. 12, 2011

(54) OPTICAL PRESSURE MONITORING SYSTEM

(75) Inventors: James A. Malmstrom, Kaysville, UT (US); Kent F. Beck, Layton, UT (US); Scott D. Miles, Sandy, UT (US)

(73) Assignee: Zevex, Inc., Salt Lake City, UT (US)

( * ) Notice: Subject to any disclaimer, the term of this patent is extended or adjusted under 35 U.S.C. 154(b) by 499 days.

(21) Appl. No.: 11/549,585

(22) Filed: Oct. 13, 2006

(65) Prior Publication Data

US 2007/0151346 A1     Jul. 5, 2007

Related U.S. Application Data

(62) Division of application No. 11/103,806, filed on Apr. 11, 2005, now Pat. No. 7,121,143, which is a division of application No. 10/290,557, filed on Nov. 8, 2002, now Pat. No. 6,907,788, which is a division of application No. 09/836,852, filed on Apr. 16, 2001, now Pat. No. 6,523,414.

(51) Int. Cl.
*G01L 7/00* (2006.01)

(52) U.S. Cl. ........................................ 73/700

(58) Field of Classification Search ........................ None
See application file for complete search history.

(56) References Cited

U.S. PATENT DOCUMENTS

| | | |
|---|---|---|
| 3,978,731 A | 9/1976 | Reeder et al. |
| 3,994,599 A | 11/1976 | Southwell |
| 4,244,365 A | 1/1981 | McGill et al. |
| 4,322,978 A | 4/1982 | Fromm |
| 4,322,979 A | 4/1982 | Fromm |
| 4,373,525 A | 2/1983 | Kobayashi |
| 4,554,837 A | 11/1985 | Danby et al. |
| 4,555,949 A | 12/1985 | Danby et al. |
| 4,612,810 A | 9/1986 | Martens |
| 4,618,261 A | 10/1986 | Flanders et al. |
| 4,624,413 A * | 11/1986 | Corsette .................... 239/333 |
| 4,631,529 A | 12/1986 | Zeitz |
| 4,762,518 A | 8/1988 | Kreinick |
| 4,829,448 A | 5/1989 | Balding et al. |
| 4,833,918 A | 5/1989 | Jean et al. |
| 4,882,575 A | 11/1989 | Kawahara |
| 4,908,676 A | 3/1990 | Bedell et al. |
| 4,920,336 A | 4/1990 | Meijer |
| 4,973,309 A * | 11/1990 | Sultan ....................... 604/110 |
| 5,008,556 A | 4/1991 | Mersch |
| 5,029,621 A | 7/1991 | Lewis |
| 5,098,380 A | 3/1992 | Aizawa et al. |

(Continued)

FOREIGN PATENT DOCUMENTS

EP            0145836         6/1985

(Continued)

*Primary Examiner* — Nicholas D Lucchesi
*Assistant Examiner* — Pritesh Patel
(74) *Attorney, Agent, or Firm* — Bateman IP Law Group (57) ABSTRACT

An optical pressure monitoring system includes a tube from an infusion set and an optical signal sensor disposed to detect changes in the diameter of the tube and thereby determine pressure changes within the tube. By selecting the position of the tube relative to the optical signal emitter and optical signal receiver, the optical signal sensor can both detect pressure changes and provide an integrity check for both the functioning of the optical signal sensor and the placement of the tube. By modifying the tube to exaggerate changes in tube diameter responsive to pressure changes, the sensitivity of the optical signal sensor can be increased.

18 Claims, 4 Drawing Sheets

U.S. PATENT DOCUMENTS

| | | | |
|---|---|---|---|
| 5,176,631 A | | 1/1993 | Koenig |
| 5,181,912 A | * | 1/1993 | Hammett .................. 604/110 |
| 5,260,665 A | | 11/1993 | Goldberg et al. |
| 5,305,237 A | | 4/1994 | Dalrymple et al. |
| 5,320,503 A | | 6/1994 | Davis |
| 5,445,622 A | | 8/1995 | Brown |
| 5,657,000 A | | 8/1997 | Ellingboe |
| 5,672,887 A | * | 9/1997 | Shaw et al. .................. 250/573 |
| 5,720,721 A | * | 2/1998 | Dumas et al. .................. 604/67 |
| 5,741,216 A | | 4/1998 | Hemmingsen et al. |
| 5,853,386 A | | 12/1998 | Davis et al. |
| 5,860,938 A | | 1/1999 | Lafontaine et al. |
| 5,935,106 A | | 8/1999 | Olsen |
| 5,964,377 A | * | 10/1999 | Demarest et al. .............. 222/136 |
| 5,983,725 A | | 11/1999 | Fischer et al. |
| 5,984,149 A | * | 11/1999 | Thanisch et al. .............. 222/340 |
| 6,110,153 A | | 8/2000 | Davis et al. .................. 604/245 |
| 6,116,472 A | * | 9/2000 | Wanbaugh et al. ........... 222/340 |
| 6,290,681 B1 | | 9/2001 | Brown |
| 6,463,813 B1 | | 10/2002 | Gysling |
| 6,523,414 B1 | | 2/2003 | Malmstrom et al. |
| 6,531,708 B1 | | 3/2003 | Malmstrom et al. |
| 6,595,950 B1 | | 7/2003 | Miles et al. |
| 6,623,447 B2 | | 9/2003 | Miles et al. |
| 6,659,976 B2 | | 12/2003 | Beck et al. |
| 6,685,670 B2 | | 2/2004 | Miles et al. |
| 6,750,468 B2 | | 6/2004 | Malmstrom et al. |
| 6,852,094 B2 | | 2/2005 | Beck et al. |
| 6,907,788 B2 | | 6/2005 | Malmstrom et al. |
| 6,923,785 B2 | | 8/2005 | Miles et al. |
| 6,979,311 B2 | | 12/2005 | Miles et al. |
| 7,121,143 B2 | | 10/2006 | Malmstrom et al. |
| 2003/0125674 A1 | | 7/2003 | Cise et al. |
| 2004/0220542 A1 | | 11/2004 | Cise et al. |
| 2005/0119625 A1 | | 6/2005 | Miles et al. |
| 2005/0178206 A1 | | 8/2005 | Malmstrom et al. |
| 2005/0209552 A1 | | 9/2005 | Beck et al. |
| 2006/0058740 A1 | | 3/2006 | Cise et al. |

FOREIGN PATENT DOCUMENTS

| | | | |
|---|---|---|---|
| EP | 0 261 850 A2 | | 3/1988 |
| EP | 0 261 860 | | 3/1988 |
| EP | 0410187 | | 1/1991 |
| GB | 2117512 | | 10/1983 |
| JP | S56-31758 | | 3/1981 |
| JP | S58-163860 | | 10/1983 |
| JP | H02-01805 | | 8/1990 |
| JP | 9-314001 | * | 12/1997 |
| WO | WO 9804301 | | 2/1998 |

* cited by examiner

OPTICAL PRESSURE MONITORING SYSTEM

The present application is a divisional application of, and incorporates by reference in its entirety, U.S. patent application Ser. No. 11/103,806, filed Apr. 11, 2005, U.S. Pat. No. 7,121,143, which is a divisional application of U.S. patent application Ser. No. 10/290,557, filed Nov. 8, 2002, U.S. Pat. No. 6,907,788, which is a divisional application of U.S. patent application Ser. No. 09/836,852, filed Apr. 16, 2001, Pat. No. 6,523,414.

BACKGROUND OF THE INVENTION

1. Field of the Invention

The present invention relates to systems for feeding solutions to patients. More particularly, the present invention relates to a system and method for monitoring fluid pressures to ensure that the solution is properly fed to the patient by the enteral feeding pump or similar device. Specifically, the invention relates to the use of optical pressure sensors to monitor fluid pressures and the presence of occlusions in the delivery set which may interfere with solution flow to the patient, and so that operation of the enteral feeding pump may be modified to compensate for the pressure and/or occlusion and thereby provide highly accurate solution delivery.

2. State of the Art

There are numerous situations in which a solution must be fed to a patient over a period of time. In some situations, the solution is provided directly into the blood stream of the patient. Saline solutions and medications supplied in such a manner are typically referred to as parenteral solutions. Because parenteral solutions are often necessary to hydrate the patient, or supply needed medications, occlusion of the infusion delivery set can be particularly dangerous to the patient. Thus, it is important to ensure that occlusions are not impeding solution flow. However, parenteral solutions typically have a very low viscosity in order to faciliate absorption into the blood stream. Therefore, the risk of occlusion of the infusion set is relatively small so long as the tube is not pinched shut by folding or some other external application of force.

In contrast to a parenteral system, an enteral feeding system is used to provide nutrient solutions to patients who, for one reason or another, are unable to eat for themselves. Such a system typically includes a pump which is attached to an input tube connected to a supply container and to an output tube which is connected to a patient. The pump draws nutrient solution from the supply container and delivers the solution to the patient. By adjusting the number of rotations of the motor, or the frequency of rotations, in the pump, an enteral feeding pump can adjust its output to deliver a predetermined amount of nutrient solution (or even medication) at a desired rate.

A significant problem with currently available enteral feeding systems, is that the intake and output tubes may become occluded. Unlike parenteral solutions, enteral feeding solutions have a relatively high viscosity, as they must carry sufficient nutrition to sustain the patient. Occlusion can occur, for example, if a fibrous substance is included in the enteral feeding solution and somehow combines to interfere with flow through the tube. Occlusion can also occur if a tube is bent sufficiently to interfere with flow therethrough, or if a roller clamp (as is commonly used for intravenous applications) is not sufficiently opened. Because of the viscosity of the solution, the amount of kinking of the tube or other interference required to interfere with solution flow is significantly less than that required in a parenteral infusion set.

If the intake tube becomes occluded, insufficient solution may be supplied to the pump, and thus to the patient. If the output tube becomes occluded, the flow of solution may be blocked, or the solution may be suddenly delivered at unusually high pressures. Additionally, medical personnel may fail to notice that the supply container is out of solution, or may not properly mount the intake and/or output tubes in the pump, thereby preventing the proper amount of solution from being delivered to the patient. Any of these scenarios can have tragic consequences if allowed to continue for a prolonged period of time.

Yet another concern with enteral feeding systems is that of viscosity of the solution and viscosity changes as a container full of solution is pumped to a patient. Knowing the viscosity of the fluid being pumped through the enteral feeding system is important because different viscosities are pumped at different rates by the enteral feeding pump. For example, a lower quantity of a highly viscous solution will be pumped by a given number of rotations of the enteral feeding pump motor than will be moved by the same pump when the solution has low viscosity. In other words, the amount of solution fed to the patient can differ substantially depending on the solution's viscosity. Thus, unless the pump is able to accurately determine and compensate for viscosity changes in the solution (i.e. by increasing or decreasing the rotations of the pump rotor in a given period of time), it is difficult to know exactly how much of the solution has been fed to the patient.

To overcome these concerns, there is a need for a system and method for determining flow discrepancies due to occlusions, viscosity (including changing viscosity) and/or improper fitting of pumps and intake/output tubes so that patients will not be endangered, and so that the proper amount of fluid will be delivered to the patient.

U.S. Pat. No. 5,720,721 (Feb. 24, 1998), which is expressly incorporated herein, provides a significant improvement in monitoring for enteral feeding pumps. The invention uses two pressure sensors to monitor viscosity and occlusions, and to enable the enteral feeding pump to compensate for the varying amount of solution which will pass through the pump with each rotation of the rotor. The pressure sensors engage the elastic tube of the infusion set and monitor changes in the strain on the infusion set by occlusions and viscosity changes. The strain information can then be processed by the pump and adjustments made to the number of rotations of the pump rotor to compensate. In the event that the occlusion is too severe to compensate by modification of the rotor rotations, the pump is shut down and an alarm signal generated so that replacement tubing may be provided.

While the pressure sensor system of U.S. Pat. No. 5,720,721 is a significant improvement over the art, it does have limitations. The pressure sensors described in the '721 patent are relatively expensive and must be properly mounted in the pump. Additionally, the person loading the pump must make sure that the upstream and downstream portions of the infusion set are properly loaded in the pump housing so that they engage the pressure sensors in the proper manner. Failure to properly load the infusion set can interfere with the functioning of the pressure sensors.

One manner for decreasing the costs of pressure sensors is to use optical sensors. While there are several methods for using optical sensors to determine the presence of occlusions, each has significant drawbacks. Some methods only allow the mechanism to determine when the pressure exceeds a certain threshold. This is done by detecting when the expanding tube of the infusion set engages a surface, thereby modifying reflection or refraction of light. Other methods require complex calculations of refraction indexes or otherwise provide relatively limited information on small pressure changes. Additionally, some methods can vary based on the material from which the infusion set is formed, or based on whether the tube of the infusion set is opaque or transparent.

In addition to the above, many mechanisms for monitoring pressure within an infusion set lack an inherent failure detector. For example, if a sensor is configured to sense only when the expanding infusion set tube engages a transparent surface, the failure to record a reflected signal may mean that the tube has not expanded. In certain situations, however, the lack of reflected signal could also mean that the sensor has failed and is either not sending the signal or is not receiving the reflected signal.

Thus, there is a need for an improved optical pressure monitoring system and method of use. Such an optical pressure monitoring system should be relatively inexpensive and easy to use. It should also provide highly accurate determination of pressure changes which indicate occlusions and/or viscosity changes. Furthermore, it should enable the use of infusion sets made from a variety of materials and without regard to whether the infusion set is formed of a tube which is transparent or opaque.

SUMMARY OF THE INVENTION

Thus, it is an object of the present invention to provide an improved method for monitoring viscosity and/or occlusions in an infusion set.

It is another object of the present invention to provide such a method which monitors viscosity and occlusions with an optical sensor system.

It is another object of the present invention to provide such a method in which the material used to form the infusion set does not interfere with proper pressure monitoring.

It is yet another object of the present invention to provide such a method in which the transparency or opaqueness of the solution does not interfere with proper pressure monitoring.

It is still another object of the present invention to provide an optical pressure sensor system with enhanced sensitivity.

It is still another object of the present invention to provide such a sensor system which checks the integrity of the sensor and which ensures that the infusion set is properly loaded in the sensor system.

The various objects set forth above and other objects of the invention are realized in specific illustrated embodiments of an optical pressure monitoring sensor system for monitoring occlusions and viscosity. It will be appreciated that all embodiments set forth may not accomplish all objects of the invention, but that preferred embodiments will accomplish a number of the objects and thereby provide an improvement over the prior art discussed above.

The optical pressure monitoring system typically includes at least one optical pressure sensor having an optical signal emitter and an optical signal receiver. (As used herein, it should be understood that the optical signal emitter is intended to cover electromagnetic radiation, regardless of whether it falls within the range visible to the human eye.) The optical signal transmitter and the optical signal receiver are generally placed on opposing sides of the tube of the infusion set. As the tube expands and contracts due to increases or decreases in pressure, the amount of light (or radiation) received by the optical signal receiver increases or decreases at a known ratio—thereby indicating the pressure within the infusion set.

In accordance with another aspect of the present invention, the tube of the infusion set is positioned between the optical signal emitter and the optical signal receiver so that it will always partially obstruct light flow between the emitter and the receiver. In such a configuration, the optical sensor ensures the infusion set has been loaded properly. If the infusion set is not properly positioned, a greater amount of light will be received by the optical signal receiver. The sensor system can then generate an alarm that the infusion set is not properly loaded in the pump.

In accordance with another aspect of the present invention, the tube of the infusion set is positioned between the optical signal emitter and the optical signal receiver so that the tube will not completely occlude light from the optical signal emitter from being received by the optical signal receiver when the solution within the tube is within acceptable operating ranges. In such a configuration, the sensor system is able to conduct a continuous integrity check. If the optical signal receiver has stopped indicating receipt of light, the lack of a signal will indicate that there has been a sensor system failure and the sensor should be replaced. The failure may be either due to a faulty optical signal emitter which is not emitting the optical signal, or a faulty optical signal receiver which is not detecting the signal sent. Either way, the patient is promptly informed of the failure and can have the sensor replaced.

In the alternative, if the infusion set is positioned to allow complete occlusion of light when the pressure in the infusion set exceeds an acceptable threshold, the alarm signal can be used to signal an occlusion which must be dealt with promptly. If light is still not being received once the infusion set has been removed from the sensor, the patient or technician will know that the sensor is not working and must be repaired or replaced.

Between the two extremes of receiving a full optical signal and no optical signal, the signals generated by the optical signal receiver indicate the extent to which the optical signal sent by the optical signal emitter have been obstructed by the tube. The enteral feeding pump, etc., can convert the measured obstruction into a determination of the pressure within the enteral feeding pump, and the tubing of the infusion set expands in a known proportion to pressure increases. The pressure calculations received can then be converted into information regarding the presence of occlusions and the viscosity of fluid within the infusion set.

With the presence of occlusions and the viscosity of fluid within the infusion set determined, the rotations of the pump may be altered (i.e. increased or decreased) to ensure that the desired amount of solution is infused to the patient. If the pressures detected are outside of acceptable ranges, the pump can be shut down and a signal generated indicating a need to replace the infusion set.

While the monitoring of the tube diameter described above provides improvements over the prior art, it has been found that yet additional improvements in sensitivity can be achieved. In accordance with one aspect of the present invention, a portion of the infusion set tube is made with a thin-walled portion. The thin-walled portion exaggerates tube expansion and contraction due to increases and decreases in pressure. The exaggerated expansions and contractions exaggerate the effect on obstruction of the light transmitted between the optical signal emitter and the optical signal receiver, thereby providing increased sensitivity to changes in the pressure within the infusion set. The voltage change which is caused by the change in light obstruction can, in turn, be converted into more detailed information regarding occlusions and viscosity within the infusion set.

In accordance with another aspect of the invention, a portion of the infusion set is disposed within a jacket. The jacket has an opening on one side through which the tube of the infusion set is visible. On the opposing side of the tube of the infusion set, the jacket is generally solid and restricts the expansion of the tube. As the pressure in the infusion set increases, the expansion of the tube within the jacket is exaggerated at the opening in the jacket because of the restriction caused by the rest of the jacket. This exaggerated expansion increases the sensitivity of readings obtained by the sensor, as the obstruction of light transmission between the emitter and the receiver is enhanced due to the increased movement in the tube wall.

In accordance with another aspect of the present invention the tube of the infusion set is disposed in a generally planar orientation. A portion of the tube is deflected out of the planar orientation by a projection. The projection is typically disposed on a side of the infusion set opposite from the portion of the wall disposed between the optical signal emitter and the optical signal receiver. The projection causes an exaggeration in the expansion and/or contraction of the side of the tube of the infusion set disposed between the optical signal emitter and the optical signal receiver, thereby rendering the sensor more sensitive to pressure changes. Further enhancements in sensitivity can be obtained by controlling the configuration of the projection and the manner in which the projection engages the tube of the infusion set.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Referring to FIG. 1, there is shown a fragmented side view of a tube 4 of an infusion set. The tube 4 is disposed so that its lower portion 4a is positioned between an optical signal emitter 8 and an optical signal receiver 12. Together, the optical signal emitter 8 and the optical signal receiver 12 form an optical sensor, generally indicated at 16.

Figure 1A:
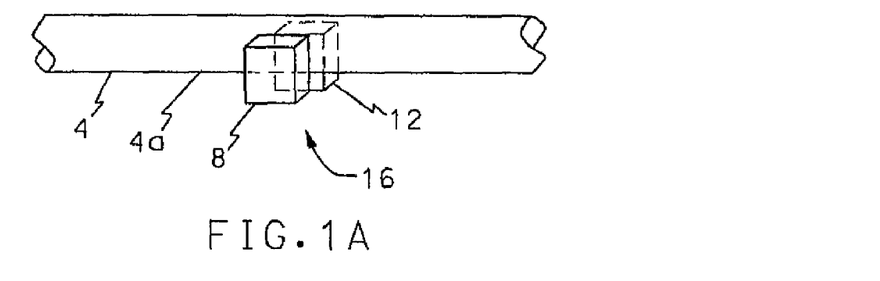
FIG. 1A shows a side, fragmented view of a tube of an infusion set passing through an optical sensor in accordance with the principles of the present invention.

The tube 4 of the infusion set is formed from a generally elastomeric material such as silicone. However, as set forth below, other materials may be used.

The tube 4 is preferably positioned so that when it is in its smallest state, the lower portion 4a still partially obstructs light transmitted between the optical signal emitter 8 and the optical signal receiver 12. As will be discussed in detail below, having the lower portion 4a of the tube 4 continually obstruct light transmission between the optical signal emitter 8 and the optical signal receiver 12 provides an important integrity check on the system by ensuring that the tube is properly loaded in the optical sensor 16.

For a tube 4 of an infusion set which is positioned down stream of the pumping mechanism, the lower portion 4a of the tube can be positioned such that it is slightly occluding the light between the optical signal emitter 8 and the optical signal receiver 12 when at ambient pressure. This is because any occlusion or viscosity increase down stream from the pump mechanism (not shown) will increase pressure, causing the tube 4 to expand and move the lower portion 4a downwardly between the optical signal emitter 8 and the optical signal receiver 12. In virtually all scenarios, the portion of the tube 4 downstream from the pump rotor will be at least as large as its ambient state.

In contrast, a portion of the tube 4 which is positioned above the pump rotor will have a vacuum generated within the tube with each rotation (or other actuation) of the pump mechanism. This vacuum is amplified by an upstream occlusion or high viscosity. Thus, a portion of the tube 4 positioned upstream from the pump rotor will partially collapse or have a reduced diameter with each rotation of the pump rotor. Thus, to keep the tube 4 in a position in which it will partially obstruct light between the optical signal emitter 8 and the optical signal receiver 12, an upstream portion of the tube will need to have the lower portion 4a placed more deeply into the optical signal sensor 16 to ensure that the it continually obstructs light flow between the optical signal emitter 8 and the optical signal receiver 12. Of course, because occlusions are manifest by a vacuum within the upstream portion of the tube 4, the upstream portion will rarely expand beyond its ambient state.

Positioning the tube 4 so that it is always at least partially between the optical signal transmitter 8 and the optical signal receiver 12 provides an important integrity check for the system. If the lower portion 4a of the tube 4 is not initially positioned to partially obstruct light, a reading by the optical signal sensor 16 that there is no light obstruction can mean two things. First, it could mean that the tube 4 is not expanding beyond some predetermined threshold to cause it to enter the optical sensor. Second, it could mean that the tube 4 of the infusion set was never loaded into the pump in the first place. However, by keeping the lower portion 4a of the tube 4 of the infusion set within the optical signal sensor 16, the ambiguity of the signal can be eliminated. If the optical signal receiver 12 detects no obstruction of light between the optical signal emitter 8 and the optical signal receiver 12, the tube 4 has not been loaded properly.

Unfortunately, it is not uncommon for health care workers and patients to be distracted while placing the infusion set into the pump. If the infusion set is not loaded properly, the solution may not be pumped to the patient, and the patient may be deprived of needed nutrients and/or medication.

In the alternative, the patient or a health care worker may have already opened a clamp on the infusion set which prevents flow prior to loading of the infusion set in the pump. If the infusion set has been inserted into the catheter in the patient, but not properly loaded into the pump, the solution may be flowing freely under the force of gravity into the patient at a rate far in excess of that desired. For some patients, this free-flow situation can raise serious health concerns, as the patient's body may not be able to handle the sudden "flood" of solution. This is especially true if the solution is medicated.

By having the tube 4 properly positioned with the optical signal sensor 16, both the patient and the health care worker can be assured that the flow of solution is being controlled by the enteral feeding pump.

In addition to always keeping the lower portion 4a of the tube 4 at least partially within the optical signal sensor 16, it is also desirable that the tube not be positioned so that it will completely obstruct light transmission between the optical signal emitter 8 and the optical signal receiver 12 during normal operation. By having the tube 4 positioned to always allow some light flow between the optical signal emitter 8 and the optical signal receiver 12, an integrity check on the optical signal sensor is made each time a reading is processed. If some light is being received by the optical signal receiver 12, then the sensor 16 must be working. If no light is being received, the optical signal sensor 16 has malfunctioned and an alarm is generated.

Those skilled in the art will appreciate that a virtual total obstruction of light transmission between the optical signal emitter 8 and the optical signal receiver 12 could also be used to determine when the infusion set has an occlusion or excessive viscosity. However, in such a scenario, an ambiguous alarm is created which could mean excessive pressure or a faulty sensor. In any event, if the pump detects an occlusion, an improper loading of the tube 4 of the infusion set, or a faulty optical signal sensor 16, the pump will generate one or more alarms and provide notice of the problem. The patient or health care worker may then correct the problem and restore the solution flow to the desired level.

Figure 1B:
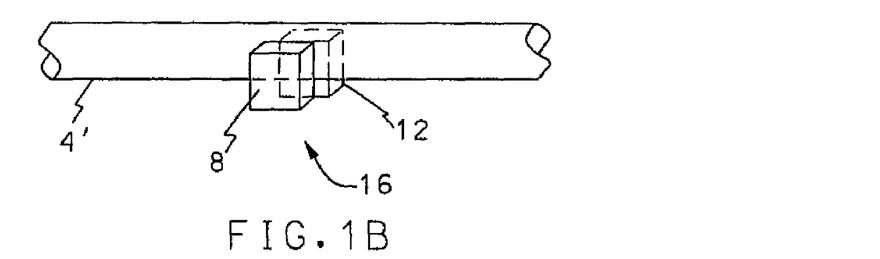
FIG. 1B shows a side view of the infusion set tube and the optical sensor of FIG. 1A, wherein the infusion set tube has expanded in diameter due to increased viscosity or an occlusion within the tube.

Turning now to FIG. 18, there is shown a side view of the infusion set tube 4 positioned between the optical signal emitter 8 and the optical signal receiver 12. Typically, the optical signal emitter 8 and the optical signal receiver 12 are positioned immediately adjacent to the tube 4. Preferably, both upstream and downstream portions of the tube 4 will be disposed in optical signal sensors 16 positioned near the pump mechanism to monitor pressure changes due to occlusions and viscosity. Thus, the pump will be able to detect both upstream and downstream occlusions and changes in viscosity which may interfere with delivery of the predetermined amount of solution.

As shown in FIG. 1B, the optical sensor 16 is positioned on a downstream portion of the tube 4. With each rotation of the pump rotor, solution is forced down the tube 4, causing a short pressure increase and expansion of the tube. If the viscosity of the solution changes significantly or there is an occlusion, the amount of pressure increase and/or its duration will change. FIG. 1B shows a tube 41 which has increased in diameter due to an occlusion downstream from the sensor. By monitoring the extent of the increase in tube size, the effect of any occlusions can be determined. While some partial occlusions may effect flow relatively little, an occlusion can also significantly impair solution flow and can cause the solution to be delivered to the patient at an undesirably high pressure. Thus, if the optical sensor 16 detects a pressure increase above a predetermined threshold, an alarm will be generated indicating that the infusion set should be checked. If the pressure detected by the optical signal sensor 16 is so high as to present safety concerns, the pump can be shut down until it has been checked.

Figure 1C:
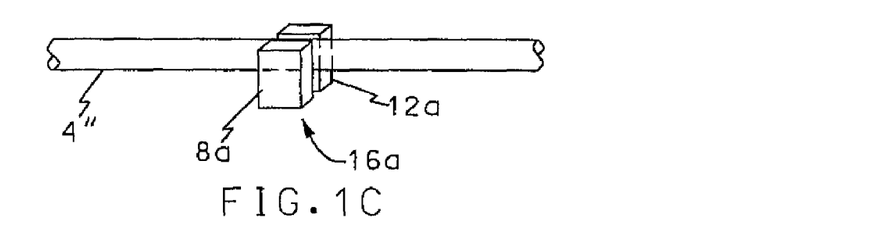
FIG. 1C shows a side view of the tube portion and optical sensor of FIG. 1A, with the tube portion being contracted in response to decreased pressure caused by an occlusion or viscosity within the infusion set.

FIG. 1C shows an upstream portion of the tube 4" positioned between an optical signal emitter 8a and an optical signal receiver 12a. Unlike the downstream portion of the tube 4', the upstream portion of the tube 4" will generally have a vacuum created therein with each rotation of the pump rotor (or other actuating movement of the pump mechanism). Thus, the tube 4" in FIG. 1C is smaller in diameter than the tube 4 in FIG. 1A and much smaller in diameter than the tube 4' in FIG. 1B.

While each rotation of the rotor will cause the tube 4" to temporarily shrink in diameter, the presence of occlusions or high viscosity can amplify the shrinking and require additional time for the tube to return to its normal diameter. If the tube has not returned to its normal diameter by the time the pump conducts its next rotation, there will be less solution in the tube for movement by the tube, and each rotation of the pump rotor will deliver less solution than when the solution is at normal pressure. By monitoring the upstream pressure in the infusion set, however, the pump can increase the number or frequency of rotations (or other actuating notion) to compensate for the pressure changes, and thereby ensure that the proper amount of solution is being delivered to the patient. If the occlusion or viscosity is causing too much impediment to solution flow through the tube 4", the pump can generate an alarm, thereby informing the user or health care worker that the infusion set must be checked.

As with the downstream optical signal sensor 16, the upstream optical signal sensor 16a can fail. Likewise, the tube 41' of the infusion set can be loaded improperly. Thus, it is preferred to have the tube 4" always obstruct some, but not all, of the light flow between the optical signal emitter 8a and the optical signal receiver 12a.

Figure 1D:
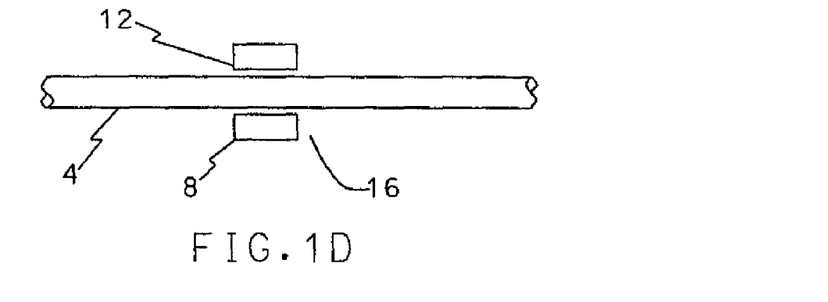
FIG. 1D shows a top view of the infusion set tube and the optical sensor of FIG. 1A.

Turning now to FIG. 1D, there is shown a top view of the infusion set tube 4 and the optical signal sensor 16 of FIG. 1A. In such an embodiment it is preferred that the optical signal emitter 8 and the optical signal receiver 12 are positioned immediately adjacent the tube 4 of the infusion set. While the optical signal emitter 8 and the optical signal receiver 12 need not touch the tube 4, having the two sensors constrict radial expansion on the sides of the tube will cause increased expansion of the tube vertically, thereby amplifying the changes caused by pressure.

Figure 1E:
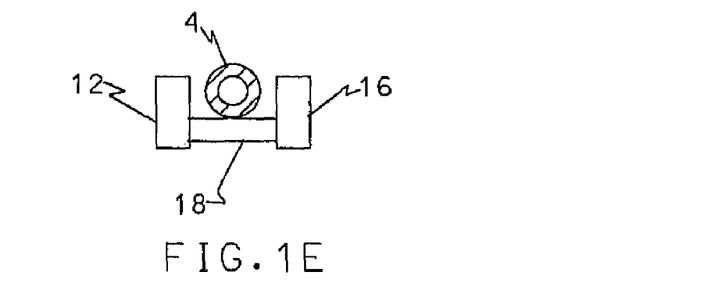
FIG. 1E shows an end view of the optical sensor and a cross-sectional view of the infusion set tube shown in FIG. 1A.

FIG. 1E shows a cross-sectional view of the tube 4 and an end view of the optical signal emitter 8 and the optical signal receiver 12. From this view, it is apparent that radial expansion of the tube 4 will interfere with transmission of optical signals, represented by arrows 18, between the optical signal emitter 8 and the optical signal receiver 12. The extent to which the tube 4 interferes with the light transmission is proportional to the pressure changes which occur within the tube during operation of the pump. It is not proportional to, the reflective index of the material or whether the material is clear or opaque. Thus, a variety of materials could be used for the tube 4 if desired.

Figure 2A:
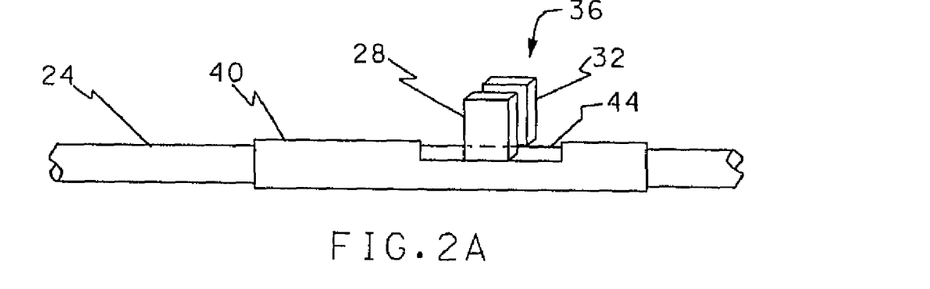
FIG. 2A shows a side view of an infusion set passing through an alternate embodiment of an optical sensor system in accordance with the principles of the present invention, in which a retaining jacket is used along the infusion set tube to amplify changes in tube diameter responsive to pressure changes within the tube.

FIG. 2A shows a side view of a infusion set 24 passing through an alternate embodiment of an optical sensor system 36 in accordance with the principles of the present invention. Disposed along the tube 24 of the infusion set is a jacket 40. While the tube 24 of the infusion set is formed from a radially expandable material such as silicone, the jacket 40 is formed from a generally rigid material that will have minimal if any radial expansion in the pressure range typically associated with solution feeding systems.

In the top of the jacket 40 is a window 44. The window 44 exposes a portion 24a of the tube 24 of the infusion set. Because the jacket 40 constricts expansion of the tube 24, expansion created by changes in the tube are amplified in the portion 24a of the tube adjacent the window. By having the optical signal emitter 28 and the optical signal receiver 32 disposed on opposing sides of the window 44, the pressure changes within the infusion set can be more accurately determined due to the amplification created by the jacket 40.

Figure 2B:
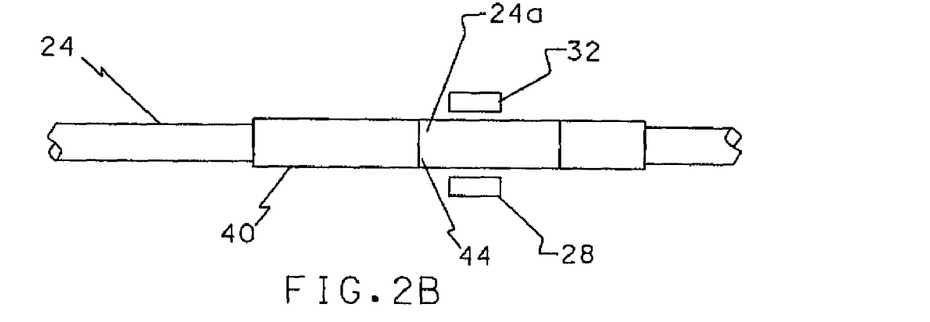
FIG. 2B shows a top view of the infusion set and optical sensor system of FIG. 2A.

Turning now to FIG. 2B, there is shown a top view of the infusion set, including the tube 24 and the jacket 40. The optical signal emitter 28 and the optical signal receiver 32 of the optical signal sensor 36 are disposed on opposing sides of the window 44 in the jacket so as to monitor the rise and fall of the portion 24a of the tube 24 exposed by the window 44.

Figure 2C:
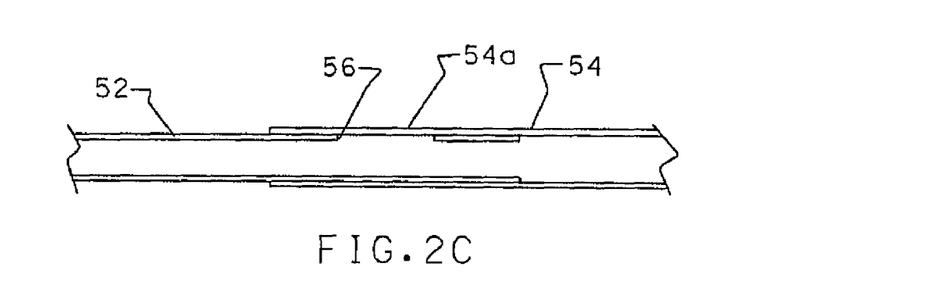
FIG. 2C shows a side cross-sectional view of another embodiment of the present invention which operates on principles similar to that of the embodiment shown in FIGS. 2A-2B.

FIG. 2C shows a cross-sectional view of an alternate embodiment of the present invention, which operates in substantially the same manner as the embodiment shown in FIGS. 2A and 2B. Instead of having a jacket, however, the infusion set, generally indicated at 50, has a rigid tube 52 and a radially expandable tube 54. The rigid tube 52 has an opening or window 56 which is covered by a portion 54a of the radially expandable tube 54. As with the portion 24a in FIGS. 2A and 2B, the portion 54a tends to expand to a greater degree than the remainder of the tube 54 because the rigid tube 52 constricts expansion in all but one direction. Thus, placing the optical signal sensor (not shown in FIG. 2C) adjacent the portion 54a of the tube 54 provides improved sensitivity.

Figure 3:
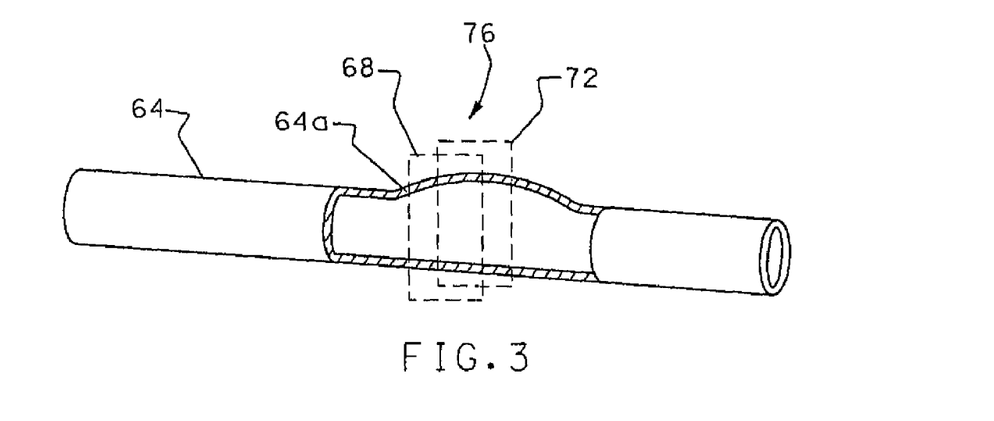
FIG. 3 shows a side, partial cross-sectional view of yet another embodiment of the present invention in which the tube of the infusion set has a thin-walled portion.

Turning now to FIG. 3, there is shown a side, partial cross-sectional view of yet another embodiment of the present invention. The infusion set 60 includes a tube 64 disposed between the optical signal emitter (shown in shadow 68) and the optical signal receiver (shown in shadow 72) of the optical signal sensor 76. The portion 64a of the tube 64 disposed between the optical signal sensor 76 has a thin-walled portion on one side. Preferably, the thin-wall portion is between 0.025 and 0.050. The outer circumference of the tube 64 and will be between 0.175 and 0.300 thinner than the normal thickness of the tube 64. As pressure within the tube 64 changes, the thin-walled portion 64a will expand and contract to a greater extent. The exaggerated expansion and contraction provides increased sensitivity to pressure changes, as the optical signal sensor 76 can more readily detect pressure changes due to the exaggerated movement.

Figure 4A:
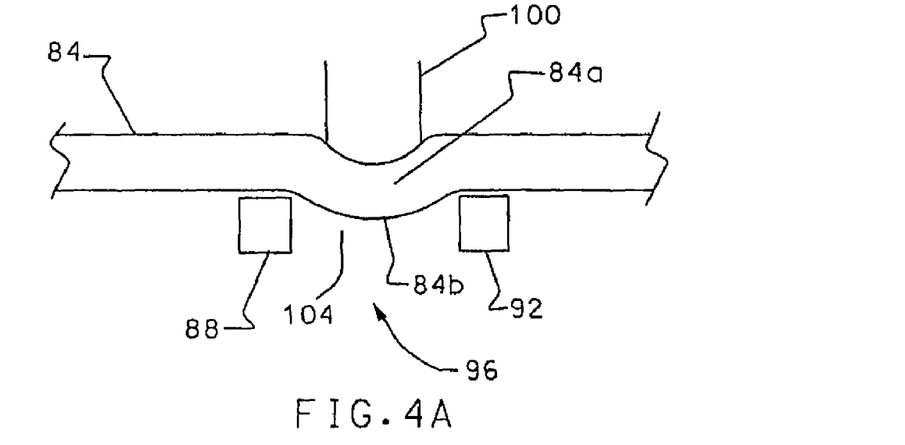
FIG. 4A shows a side view of yet another embodiment of an optical sensor system made in accordance with the present invention and a portion of the tube of an infusion set passing therethrough.

Turning now to FIG. 4A, there is shown a side view of yet another embodiment of an optical sensor system made in accordance with the present invention and a portion of the tube of an infusion set passing therethrough. The tube 84 is disposed generally above an optical signal emitter 88 and an optical signal receiver 92 which form an optical signal sensor, generally indicated at 96.

The tube 84 is positioned in a generally planar configuration. However, a portion 84a of the tube 84 positioned above the space between the optical signal emitter 88 and the optical signal receiver 92 is engaged by an abutment member 100 so as to deflect that portion of the tube into the space 104 between the optical signal emitter 88 and the optical signal receiver 92.

The abutment member 100 serves two valuable functions. First, the abutment member 100 helps to ensure the tube 84 of the infusion set is in the desired location and helps resist movement of the tube which may be caused by the pump mechanism. Second, the abutment member 100 prevents expansion of the tube 84 along the top side thereof adjacent to the optical signal sensor 96. This causes pressure changes to expand and contract the opposing wall 84b of the tube in an exaggerated manner to show the sidewalls of the tube will normally respond to pressure changes. As with the embodiments discussed above, this exaggerated movement allows the optical signal sensor 96 to detect smaller changes in pressure, and thereby provide more accuracy in determining pressure changes within the infusion set.

Figure 4B:
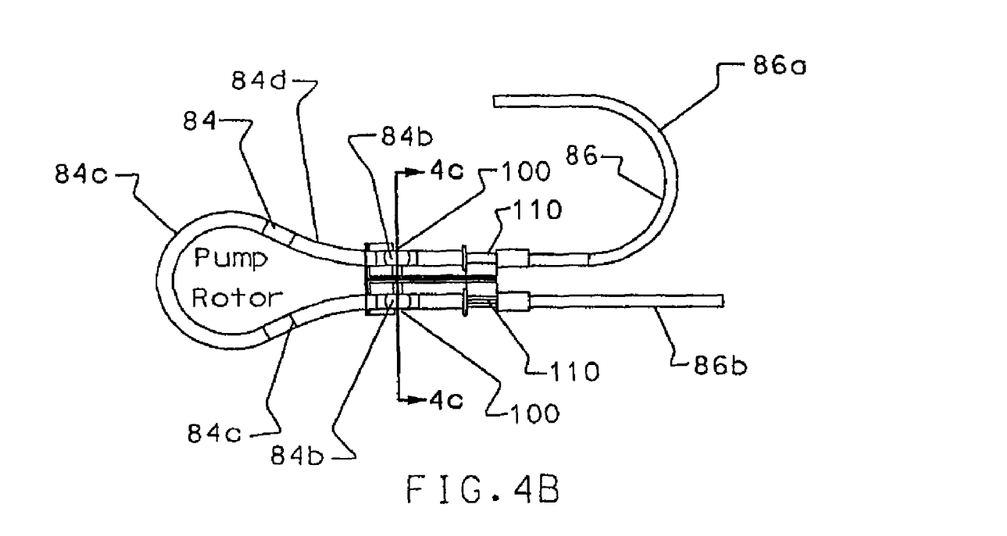
FIG. 4B shows a bottom view of an infusion set and adapter housing in accordance with the principles of the embodiment of FIG. 4A and configured for placement in an enteral feeding pump.

Turning now to FIG. 4B, there is shown a bottom view of the tube 84 of an infusion set 86 and the abutment member 100 as used in accordance with the principles of the present invention. In addition to the tube 84, the infusion set includes an upstream intake tube 86a and a downstream output tube 86b.

The tube 84 of the infusion set has a looped portion 84c which wraps around the rotor (not shown) of an enteral feeding pump, or similar device. The abutment member 100 is disposed to engage the tube 84 of the infusion set 86 both upstream and downstream from the pump rotor. As will be discussed in additional detail below, pressure is monitored both upstream and downstream from the pump rotor to ensure that 1) a known quantity of solution reaches the portion of the tube 84 which engages the pump rotor, and 2) that the solution pumped by the pump rotor reaches the patient.

The tube 84 of the infusion set 86 is typically made from an elastomeric material such as silicone. This allows the tube 84 to stretch and to expand and contract as it is worked by the pump rotor to move solution through the tube. The remainder of the infusion set 86, however, need not be formed from silicone. To the contrary, less expensive tubing can be used for the remainder of the infusion set 86. The silicone tube 84 and the remainder of the infusion set 86 are typically held together by an adaptor 108 having two connectors 110. These connectors 110 can be formed as an integral, one piece adaptor including the abutment member 100, or can be formed separately.

As the pump rotor rotates, a vacuum is created in the upstream portion 84d of the tube 84 of the infusion set. This vacuum will cause tube portion 84b along the upstream portion 84d to contract. The extent of contraction and the time necessary to return to ambient is a function of the viscosity of the solution upstream from the pump rotor and the presence of any occlusions. By monitoring the change in the diameter of the tube portion 84b upstream from the pump rotor, the enteral feeding pump is able to determine the viscosity and occlusion's effect on solution flow rate and thereby determine the amount of solution which is being pumped by each rotation of the pump rotor. This is typically done by monitoring the voltage produced by the optical signal receiver. The greater the voltage which is received, the greater the amount of light which is getting passed the tube portion 84*b*. If the monitored collapse of the tube portion 84*b* indicates that the viscosity is too great or that there is an occlusion, the voltage reading will be higher than expected and the enteral feeding pump can generate an alarm signal indicating that a predetermined threshold has been passed.

Unlike the upstream portion 84*d* of the tube 84 of the infusion set 86, the downstream portion 84*e* will receive increased pressure with each rotation of the pump rotor, thereby causing the downstream portion 84*b* to expand. The expansion will restrict light flow from the optical signal emitter to the optical signal receiver, thereby decreasing the voltage generated. If the pressure increase lasts for too long a period of time or is too great, the optical signal sensor (not shown) will produce voltage readings indicative of the excess or prolonged expansion of portion 84*b* along the downstream portion 84*e* of the tube 84. The enteral feeding pump can then generate an alarm indicating that an occlusion downstream. This will prevent the patient from being subject to sudden pressure increases which could cause discomfort or even injury.

As mentioned with respect to FIG. 4A, the abutment member 100 increases the accuracy of the optical signal sensor 96 by exaggerating the expansion (downstream) or contraction (upstream) along the tube portion 84*b*. This exaggerated movement enables the enteral feeding pump to more accurately determine pressure by the voltage readings produced by the optical signal sensor.

Figure 4C:
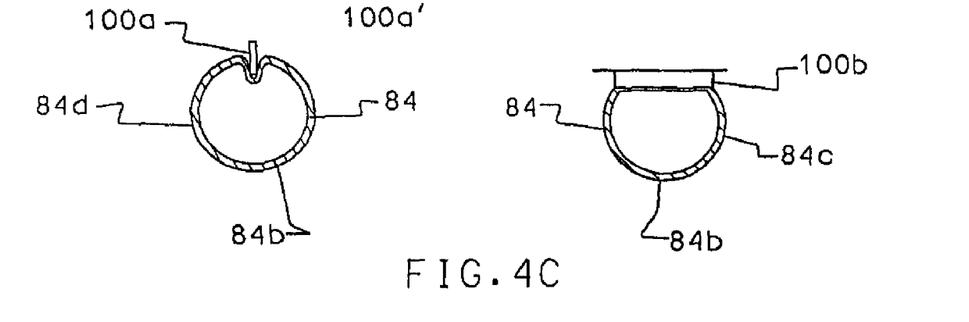
FIG. 4C shows a cross-sectional view of FIG. 4B taken along the plane 4C-4C.

Turning now to FIG. 4C, there is shown a cross-sectional view of the tube 84 of the infusion set 86, and fragmented views of the abutment members 100*a* and 100*b*. In the upstream portion 84*d* of the tube 84 of the infusion set 86, the monitored property is almost always contraction of the tube. To this end, it has been found preferable to have an abutment member 100*a* which forms a relatively narrow projection and extends into engaging contact with the exterior of the tube 84. Preferably, the end of the projection should have a thickness (i.e. a cross-section taken generally co-planar with the cross-section of the tube) with a radius which is ⅛ the diameter of the tube 84. The narrow projection formed by the abutment member 84*a* allows the outer edges of the tube 84 to move upward and downwardly. This has been found to increase sensitivity to the vacuum created within the upstream portion 84*d* of the tube 84, and thereby enables the voltage reading of the associated optical signal sensor to more accurately indicate the pressure within the tube.

Because the downstream portion 84*e* of the tube 84 generally monitors only pressures at ambient or greater, it is not necessary for the abutment member 100*b* to form such a protrusion. Rather, the abutment member 100*b* is generally broader and generally presses against the entire top of the tube 84 at the location adjacent the optical signal sensor. As the pressure in the downstream portion 84*e* of the tube 84 increases, the relatively flat abutment member 100*b* limits expansion of the tube upwardly, thereby causing exaggerated expansion on the opposing side 84*b* of the tube 84.

Figure 4D:
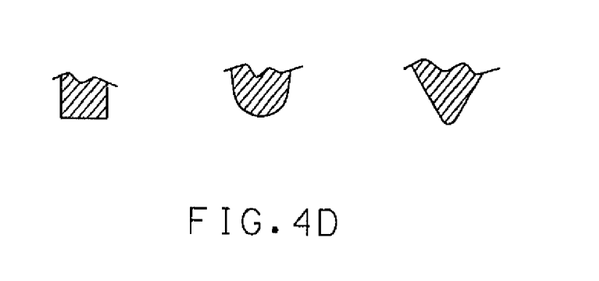
FIG. 4D shows a cross-sectional view of a number of different abutment members configurations in accordance with the present invention.

While a relatively narrow protrusion 100*a* and a broad protrusion 100*b* are shown for the abutment members, those skilled in the art will appreciate that abutment members having a variety of cross-sections may be used. For example, FIG. 4D shows the cross-section of protrusions which are generally squared, semi-oval and triangular. Through routine experimentation, those skilled in the art will be able to determine appropriate voltage curves associated with the shape and the tubing to be used.

Figure 5:
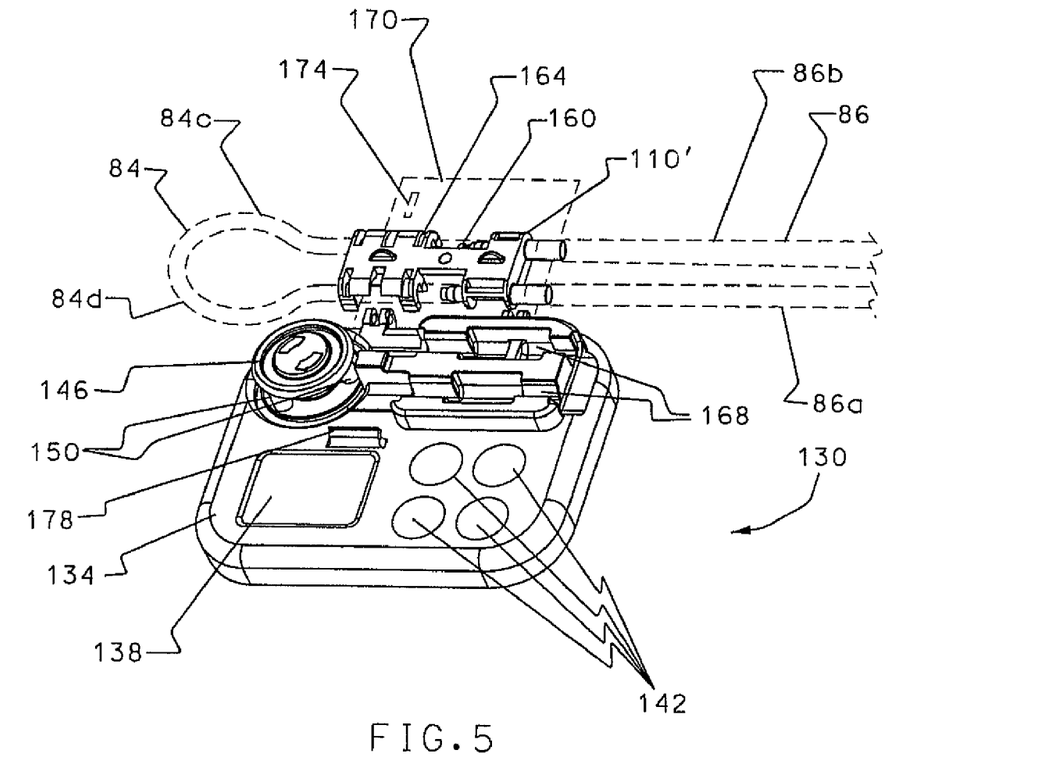
FIG. 5 shows a perspective view of an enteral feeding pump employing one embodiment of an optical sensor system in accordance with the principles of the present invention.

Turning now to FIG. 5, there is shown a perspective view of an enteral feeding pump, generally indicated at 130, formed in accordance with the principles of the present invention. The pump 130 includes a motor unit 134 with a digital readout 138 and a plurality of control buttons 142. The motor unit 134 controls a rotor 146, which has a plurality of rollers 150 (typically three) which are configured to engage the tube 84 of the infusion set 86.

As the rotor 146 rotates, the rollers 150 selectively pinch off the tube 84 and push solution contained therein downstream. If no pressure changes where present, one could readily determine the amount of solution moved by the pump 130 by simply counting the rotations. The pressures within the infusion set 86, however, effect the amount of solution which is moved by each rotation of the rotor 146. By determining these pressures, one can quite accurately calculate the amount of fluid being pumped. Thus, it is important to track the upstream and downstream pressures in the infusion set 86.

As shown in FIG. 5, the connectors 1101 which connect the intake tube 86*a* and output tube 86*b* of the infusion set 86 to the tube 84 are formed integrally with an anti-free flow device 160 which is disposed within the tube 84 in the form of an adaptor housing 164 which nests within a pair of channels 168 on the enteral feeding pump 130. The housing may also have integrally formed therein one or more abutment members similar to those discussed above. In the alternative, a cover 170 which is used to hold the housing 164 to the channels 168 of the enteral feeding pump 130 may have one or more abutment members 174 formed thereon. Closing the cover 170 causes the abutment member 174 to extend through an opening in the housing 164 and to engage the tube 84. The tube 84 is then automatically and properly positioned between the optical signal emitter and the optical signal receiver (not visible in FIG. 5) which are disposed along the channels 168.

Because the abutment member 174 will push the tube 84 into a position in which the tube partially obstructs optical signals in the optical signal sensor, a high voltage signal from the sensor will indicate that the tube 84 of the infusion set is not properly loaded, and/or that the cover 170 has not been properly closed. A catch 178 can be used to hold the cover 170 closed.

By using the digital display 138 or an auditory signal, the enteral feeding pump 130 can readily determine and display the amount of solution which is being pumped during a given amount of time. It can also develop a signal when thresholds are exceeded, and can indicate trends in increased or decreased viscosity if desired. Furthermore, if the pump has been set to deliver a predetermined amount of solution in a given time, the enteral feeding pump 130 is able to adjust the rotor frequency (i.e. the number of times the rotor 146 rotates in a given amount of time) to ensure the desired amount of solution has been delivered. Thus, the present invention is able to obtain the advantages set forth in U.S. Pat. No. 5,720,721, without the need of using pressure transducers or other similar, costly devices.

By utilizing the aspects of the present invention discussed above, an optical sensor can be used to provide highly accurate pressure and viscosity information while substantially lowering the cost of the enteral feeding pump. While numerous different embodiments of the present invention have been disclosed, those skilled in the art will appreciate numerous modifications which can be made without departing from the scope and spirit of the present invention. The appended claims are intended to cover such modifications.

What is claimed is:

1. An adapter for disposition along an infusion set, the adapter comprising:
   a pumping tube for engaging a pump rotor;
   a first connector for attaching an upstream portion of an infusion set to one end of the tube;
   a second connector for attaching a downstream portion of an infusion set to a second end of the tube, the second connector being attached to the first connector; and
   an abutment member disposed adjacent to the first connector and the second connector, the abutment member contacting the tube so as to deflect a portion of the tube into a nonlinear position, the abutment member engaging one side of said tube without engaging the other side of said tube such that the other side of the tube is not contacted and is unconstrained so as to permit the other side of said tube to expand due to pressure within the tube.

2. The adapter according to claim 1, wherein the first connector is configured for receiving a tube of a known diameter at ambient pressure, and wherein the abutment member has a first portion having an end configured for engaging the tube, the first portion having an end having a cross-sectional diameter which is about ⅛th the diameter of the tube, such that the end presses inwardly into the tube when the tube is attached to the first connector.

3. An infusion set for an enteral feeding pump comprising the adapter of claim 1, and further comprising an upstream tube connected to the first connector, and a downstream tube connected to the downstream connector.

4. The adapter for disposition along an infusion set of claim 1, wherein the abutment member has a generally flat end which engages the pumping tube and flattens a portion of the tube at a first location without contacting the opposing side of the tube at said first location.

5. The adapter for disposition along an infusion set of claim 1, wherein the abutment member presses into the pumping tube to thereby minimize radial expansion of the tube in one direction while maximizing radial expansion of the tube in an opposite direction due to pressure.

6. The adapter for disposition along an infusion set of claim 1, wherein the abutment member has a rounded end.

7. The adapter for disposition along an infusion set of claim 1, wherein the abutment member has a generally v-shaped cross-section.

8. The adapter of claim 1, wherein the pumping tube is a radially expandable resilient tube which engages a pump rotor.

9. A system comprising the adapter of claim 8, and further comprising an optical emitter and an optical receiver, and wherein the radially expandable tube is positioned at least partially between the optical signal emitter and the optical signal receiver so as to increasingly occlude a varying amount of signals between the optical signal emitter and the optical signal receiver as the tube expands due to pressure in the tube.

10. The system of claim 9, wherein the abutment member disposed adjacent to one side of a section of the radially resilient tube and wherein the opposing side of said section of the radially resilient tube is unconstrained, said section of radially resilient tube being located between the optical signal emitter and the optical signal receiver such that the abutment member inhibits radial expansion of the tube in at least one direction and thereby amplifies movement of the radially resilient tube between the optical signal emitter and the optical signal receiver in response to increases in pressure within the radially resilient tube.

11. The system of claim 9, further comprising an enteral feeding pump and wherein the optical signal emitter and the optical signal receiver are disposed in the enteral feeding pump.

12. The system of claim 9, wherein the optical signal emitter and the optical signal receiver are disposed on opposing sides of the radially resilient tube.

13. An adapter for an infusion set comprising:
   a resilient tube;
   a first connector attached to a first end of the resilient tube and to an upstream portion of an infusion set;
   a second connector attached to a second end of the resilient tube and to a downstream portion of an infusion set; and
   an abutment member, the abutment member being located to engage one side of a section of the resilient tube and not the opposing side of the section of resilient tube so as to deflect the section of resilient tube into a non-linear position, wherein the resilient tube is placed in tension and held against the abutment member, wherein said opposing side of said section of resilient tube is free to expand and contract due to changes in pressure, and wherein the section of resilient tube is placed between an optical emitter and an optical detector to thereby detect changes in diameter of the section of resilient tube due to pressure.

14. A system comprising the adapter of claim 13, further comprising an optical emitter and an optical detector disposed adjacent said section of the resilient tube.

15. An adapter for an infusion set comprising:
   a resilient tube;
   first and second positioning devices for holding first and second portions of the resilient tube so as to define a length of resilient tube therebetween; and
   an abutment member located between the first and second positioning devices, the abutment member contacting one side of a section of the resilient tube without contacting an opposing side of the section of resilient tube so as to deflect the length of tube into a non-linear position whereby the resilient tube is placed in tension and held against the abutment member, wherein said opposing side of the section of resilient tube is unconstrained so as to allow said section of resilient tube to expand and contract due to pressure changes, and wherein said section of resilient tube is placed between an optical emitter and an optical detector such that changes in diameter of the resilient tube result in changes in light transmission between the optical emitter and optical detector.

16. A system comprising the adapter of claim 15, and further comprising an optical emitter and an optical detector disposed adjacent the section of the resilient tube.

17. An adapter for disposition along an infusion set, the adapter comprising:
   an elastomeric tube for engaging a pump to pump fluids therethrough;
   a first connector attached to an upstream portion of an infusion set and attached to a first end of said elastomeric tube;
   a second connector attached to a downstream portion of said infusion set and attached to a second end of said elastomeric tube;
   an abutment member disposed adjacent to the first connector and the second connector, the abutment member being configured for deflecting a portion of the elastomeric tube into a nonlinear position, the abutment member engaging one side of said tube without engaging the other side of said tube such that the other side of the tube is not contacted and is unconstrained so as to permit the other side of said tube to expand due to pressure within the tube; and wherein expansion or contraction of the side of the tube not in contact with the abutment member is detected as a change of pressure within the tube.

18. The adapter of claim 17, wherein the second connector is attached to the first connector independent of the elastomeric tube.

* * * * *